United States Patent [19]

Fields, Jr. et al.

[11] Patent Number: 5,072,033

[45] Date of Patent: Dec. 10, 1991

[54] PROCESS FOR PRODUCING N-PHOSPHONOMETHYLGLYCINE

[75] Inventors: Donald L. Fields, Jr., Manchester; Raymond C. Grabiak, Maryland Heights; Karl E. Koenig; Dennis P. Riley, both of Ballwin, all of Mo.

[73] Assignee: Monsanto Company, St. Louis, Mo.

[21] Appl. No.: 625,342

[22] Filed: Dec. 11, 1990

[51] Int. Cl.$^5$ ............................................. C07F 9/38
[52] U.S. Cl. ........................................................ 560/17
[58] Field of Search ............................................ 560/17

[56] References Cited

U.S. PATENT DOCUMENTS

| 3,950,402 | 4/1976 | Franz | 260/502.5 |
| 3,954,848 | 5/1976 | Franz | 260/502.5 |
| 4,937,376 | 6/1990 | Fields et al. | 562/16 |

FOREIGN PATENT DOCUMENTS 20356 12/1981 Hungary .
187347 2/1984 Hungary .

Primary Examiner—Bruce Gray
Attorney, Agent, or Firm—Frank D. Shearin

[57] ABSTRACT

A process for the production of N-phosphonomethylglycine comprising contacting N-phosphonomethyliminodiacetic acid with a peroxide in the presence of a catalyst selected from the group consisting of the salts and salt complexes of cobalt and vanadium, and an effective amount of a quinone or hydroquinone.

14 Claims, No Drawings

PROCESS FOR PRODUCING N-PHOSPHONOMETHYLGLYCINE

BACKGROUND OF THE INVENTION

This invention relates to a process for preparing N-phosphonomethylglycine by the oxidation of N-phosphonomethyliminodiacetic acid using a homogeneous catalyst system. More particularly, this invention relates to a process for producing N-phosphonomethylglycine by the oxidation N-phosphonomethyliminodiacetic acid using a salt of a selected metal in the presence of a quinone or quinone derivative.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-Phosphonomethylglycine and its salts are conveniently applied in an aqueous formulation as a postemergent phytotoxicant for the control of numerous plant species. N-phosphonomethylglycine and its salts are characterized by broad spectrum activity, i.e., the controlled growth of a wide variety of plants.

U.S. Pat. No. 3,950,402 to Franz discloses a process for the production of N-phosphonomethylglycine by forming an admixture of N-phosphonomethyliminodiacetic acid, water, and a metallic catalyst selected from the noble metals, heating the admixture to an elevated temperature (greater than 70 C to avoid low yields) and contacting the admixture with a free oxygen-containing gas.

U.S. Pat. No. 3,954,848 to Franz discloses a process for the production of N-phosphonomethylglycine by reacting N-phosphonomethyliminodiacetic acid with an oxidizing agent, such as hydrogen peroxide, in an aqueous acidic medium in the presence of a strong acid at a temperature of from about 70° C. to about 100° C. It is disclosed that one should employ at least 2 moles of the hydrogen peroxide for each mole of the N-phosphonomethyliminodiacetic acid, and preferably more.

Hungarian Patent Application No. 187,347 discloses a process for the preparation of N-phosphonomethylglycine by the oxidation of N-phosphonomethyliminodiacetic acid with peroxides using a catalytic amount of a metal compound selected from compounds of silver, iron, tin, lead, manganese or molybdenum. Molybdates are preferred. At temperatures lower than 80° C., usually a contaminated end product is obtained. Typically, the reaction is carried out at a temperature of above 80° C. and preferably above 100° C. at pressures exceeding atmospheric, wherein the intermediate N-oxide is decomposed as rapidly as it forms. It is further disclosed that at least two mole equivalents of peroxide should be used for each mole equivalent of N-phosphonomethyliminodiacetic acid.

Although satisfactory results are obtained by the processes of the prior art to prepare N-phosphonomethylglycine using heterogeneous catalysts such as activated carbon or a noble metal on a support, there is now provided a process for preparing N-phosphonomethylglycine using a homogeneous catalyst system which produces outstanding results through high conversions and selectivities, which minimizes the formation of undesirable by-products such as phosphates, and simplifies the separation of the product from the catalyst. The process of the present invention also achieves these results at lower pressures than the molecular oxygen gas processes of the prior art.

SUMMARY OF THE INVENTION

These and other advantages are achieved by a process for the production of N-phosphonomethylglycine comprising contacting N-phosphonomethyliminodiacetic acid with a peroxide in the presence of a catalyst selected from the group consisting of the salts and salt complexes of cobalt and vanadium, and an effective amount of a quinone or quinone derivative represented by the formulas

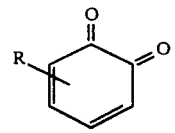

1

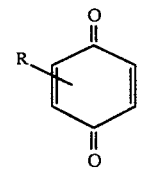

2

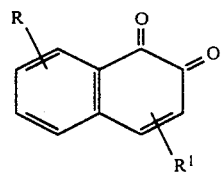

3

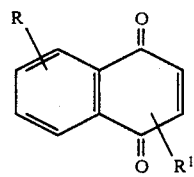

4

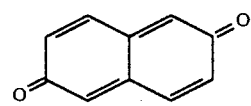

5

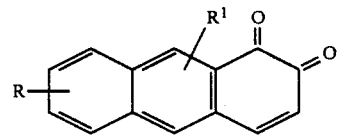

6

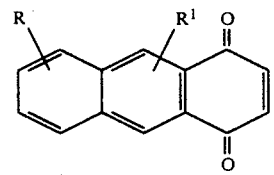

7

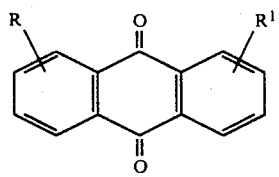

8

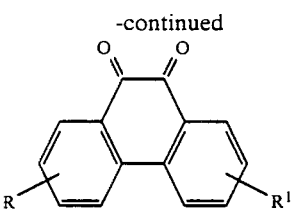  9
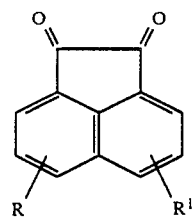  10
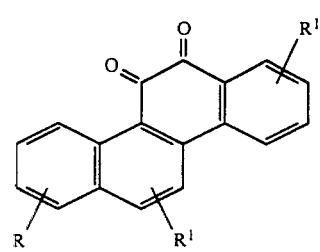  11
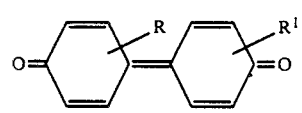  12
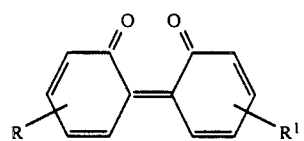  13
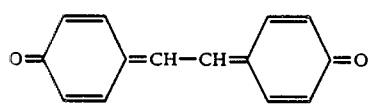  14
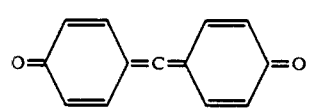  15
and the corresponding hydroquinones represented by the formulas
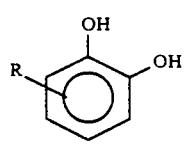  16
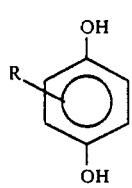  17
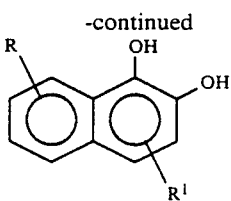  18
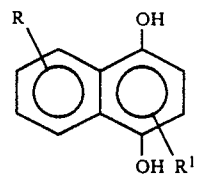  19
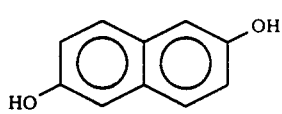  20
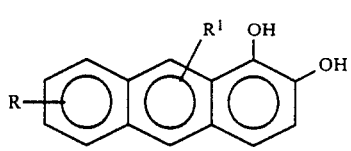  21
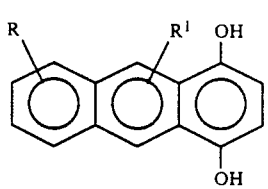  22
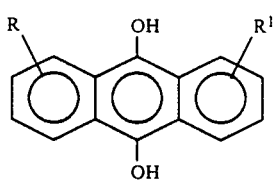  23
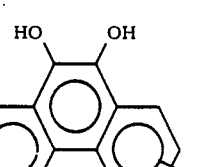  24
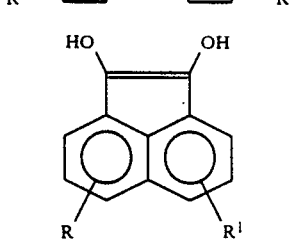  25
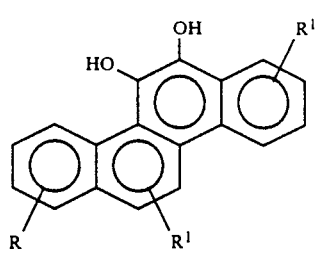  26

-continued

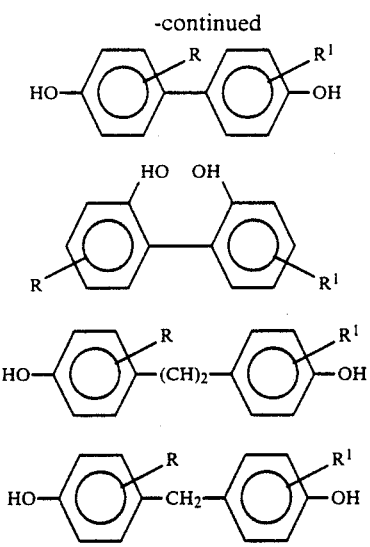

wherein R and R¹ are groups to solubilize the quinone or hydroquinone in the reaction medium.

DETAILED DESCRIPTION OF THE INVENTION

The process of the present invention involves contacting N-phosphonomethyliminodiacetic acid in a slurry or solution with a water soluble salt or a salt complex of selected metals in the presence of a quinone or hydroquinone. The mixture or solution is contacted with a peroxide while heating the reaction mass to a temperature sufficiently high to initiate and sustain the oxidation reaction of N-phosphonomethyliminodiacetic acid to produce N-phosphonomethylglycine.

The catalyst in the present invention can be any one or more of the salt and salt complexes of cobalt or vanadium. Suitable salts include cobalt sulfate, cobalt (II or III) acetylacetonate, cobalt chloride, cobalt bromide, cobalt nitrate, cobalt acetate, vanadium sulfate, vanadium bromide, vanadium chloride, and the like.

The catalyst can be added to the N-phosphonomethyliminodiacetic acid in the salt form, or the salt may be generated in situ by the addition of a source of the metal ion, such as cobalt oxide or vanadium pentoxide, which dissolves in the reaction mixture.

The concentration of the catalyst in the process of the present invention can vary within wide limits. The concentration can vary between about 1 molar to about 0.0001 molar total metal ion concentration. For most of the metal salts, the reaction appears to have a first order dependency on the catalyst concentration, i.e. the reaction rate increases linearly as a catalyst concentration increases. The preferred concentration for the catalyst metal ion is in the range of about 0.1 molar to about 0.001 molar which gives a suitably fast rate of reaction that can be easily controlled and favors selectivity to N-phosphonomethylglycine.

The quinone and quinone derivatives of the present invention are known to the art. Suitable water soluble quinone compounds include, hydroxy substituted p-benzoquinone, o-benzoquinone, p-benzoquinone, 1,4-naphthoquinone, 1,2-naphthoquinone, 2,6-naphthoquinone, 1,4,5,8-naphthodiquinone. Compounds that have been substituted with appropriate substituents to make them water soluble in the reaction mixture include dihydroquinones, stilbenequinones, 9,10-phenanthrenequinones, 1,4-phenanthrenequinones, 1,2-phenanthrenequinones, 3,4-phenanthrenequinones, 9,10-anthraquinones, 1,2-anthraquinones, 1,4-anthraquinones, 1,2-benz-910-anthraquinone(benz-[a]anthracene-7,12-dione)s, 1,2-benz-3,4-anthraquinone (benz[a]-anthracene-5,6-dione)s, 1,2, 5,6-dibenz-9,10-anthraquinone (dibenz[a,h-]anthracene-7,14-dione)s, 5,6-chrysenequinone (5,6-chrysenedione)s, and 6,12-chrysenequinone chrysenequinone(6,12-chrysenedione)s.

As will occur to those skilled in the art in view of the present disclosure, quinones or hydroquinones that are substituted on at least one of the ring structures can be used in the process of the present invention, provided that the substituted group does not interfere with the process of the present invention. Examples of groups that can be substituted on the ring structures include: halo, such as chloro or bromo; sulfonyl groups; alkyl having from one to six carbon atoms; oxyalkyl having from one to six carbon atoms; benzyl; amino; carboxy; cyano; nitro; hydroxy; phosphonic; phosphinic; phosphonium; quaternary amino groups; and the like. However, higher molecular weight quinones and hydroquinones, and anthraquinones and anthrahydroquinones, can be insoluble in the aqueous reaction medium. Accordingly, such higher molecular weight compounds, such as the anthraquinones, require substitution of a water solubilizing functional group on the molecule to aid water solubility as known to those skilled in the art. Of these, naphthaquinone, substituted anthraquinones and benzoquinones are preferred, and sulfonyl acid anthraquinone derivatives substituted with sulfonic acid groups and salts thereof are especially preferred. Other preferred compounds include 4-naphthalenediol and a sulfonic acid salt of 9,10-anthracenediol.

The concentration of the quinone and hydroquinone compounds in the process of the present invention can vary within wide limits, depending upon the catalyst salt and the amount of N-phosphonomethyliminodiacetic acid that are used, and the particular quinone or hydroquinone compound that is selected. In general, it has been found that the concentration of the quinone and hydroquinone compounds can vary from about 0.005 molar in the reaction solution to one molar, and higher concentrations of the quinone and hydroquinone compounds can be used, although such higher concentrations do not seem to have a significant effect on the selectivity of the oxidation of N-phosphonomethyliminodiacetic acid to N-phosphonomethylglycine. It has been found that concentrations of the quinone and hydroquinone compounds between about 0.01 molar to about 0.5 molar provides satisfactory results, and this is the concentration that is preferred.

The temperature of the present process can vary from as low as about 20° C. to about 100° C. Although temperatures below about 20° C. can be used, such temperatures would require the use of cooling, and no advantages are obtained. At temperatures above about 100° C., degradation is observed, which affects the final yield of the desire N-phosphonomethylglycine. Temperatures between about 20° C. and about 85° C. are preferred.

To carry out the process of the present invention, it is only necessary to bring N-phosphonomethyliminodiacetic acid together with an effective amount of the catalyst salt and an effective amount of the quinone or hydroquinone compounds in the presence of a peroxide in an aqueous solution or slurry. Any number of peroxides known to those skilled in the art can be used in the present process. Suitable peroxides include hydrogen peroxide, performic acid, peracetic acid, perbezoic acid, peroxytrifluoroacetic acid, benzoyl peroxide, benzenepersulfonic acid, and the like. Hydrogen peroxide is preferred, and it is advantageous to use hydrogen peroxide in the form of a concentrated solution, say between about 30% and 60%.

In the process of the present invention, the amount of peroxide should be the stoichiometric amount required to convert the N-phosphonomethyliminodiacetic acid to N-phosphonomethylglycine. As will occur to those skilled in the art, when less than the stoichiometric amount of peroxide is used, the yield of the desired N-phosphonomethylglycine is lower. A slight excess of peroxide can be used to insure a quantitative conversion of the N-phosphonomethyliminodiacetic acid, but there is no advantage to using large excesses of peroxide.

The initial pH of the reaction affects the reaction rate and the selectivity to N-phosphonomethylglycine. The initial pH of the reaction can vary between about pH 0.1 to about pH 7. A preferred range is from about pH 0.1 to pH 3, and a more preferred pH range is the natural pH of the N-phosphonomethyliminodiacetic acid in an aqueous solution which varies with the N-phosphonomethyliminodiacetic acid concentration and the reaction temperature.

The oxidation reaction can take place in a solution or a slurry. For a solution the initial concentration of the N-phosphonomethyliminodiacetic acid in the reaction mass is a function of the solubility of the N-phosphonomethyliminodiacetic acid in the solvent (i.e. water) at both the desired reaction temperature and the initial pH of the solution. As the solvent temperature and the initial pH change, the solubility of N-phosphonomethyliminodiacetic acid changes. It has been found that the process of the present invention works with very dilute solutions, or even with a slurry of the N-phosphonomethyliminodiacetic acid in an aqueous solution. The reaction is typically carried out in an aqueous solvent, i.e., containing at least about 50 wt.% water. The preferred aqueous solvent is distilled, deionized water.

This invention is further illustrated by, but not limited to, the following examples. Conversion is calculated by dividing the moles of other compounds produced by the moles of starting N-phosphonomethyliminodiacetic acid and multiplying by 100. Selectivity is calculated by dividing the moles of N-phosphonomethylglycine produced by the moles of N-phosphonomethyliminodiacetic acid converted and multiplying by 100.

EXAMPLES 1-3

These examples illustrate the superior results that are obtained by the process of the present invention with a vanadium catalyst.

To a 100 ml round bottomed flask equipped with a stirrer and a thermometer was added 13.5 g (0.06 mol) N-phosphonomethyliminodiacetic acid, 0.5 g vanadyl sulfate (29% H₂O), 50 g water and 0.003 mol of the additive to be screened. The mixture was heated to 80° C. where 17.5 g of 30% hydrogen peroxide (0.15 mol) was added dropwise over 30 minutes, keeping the temperature under 85° C. by the addition rate. Heating was continued at 85° C. until a color change of red vanadium +5 to blue vanadium +4 occurred (10-15 minutes). After cooling to room temperature, the solids were filtered. Both the solid and filtrate were analyzed by HPLC, and the results are reported in Table 1.

TABLE 1

| Example | Additive | Glyphosate (%) | AMPA's (%) | PO₄ (%) | Conversion (%) | Selectivity (%) |
| --- | --- | --- | --- | --- | --- | --- |
| 1 | Control No Additive | 50.8 | 19.9 | 31.7 | 98.8 | 51.5 |
| 2 | 1-Anthraquinonesulfonic acid | 75.2 | 6.3 | 9.9 | 86.5 | 86.9 |
| 3 | 2-methyl-1,4-napthoquinone | 74.4 | 4.1 | 7.0 | 84.9 | 90.0 |

EXAMPLES 4-6

The procedures of Examples 1-3 is repeated except that cobalt sulfate is used as a catalyst instead of vanadyl sulfate. Substantially the same results are obtained as reported in Examples 1-3.

Although the invention has been described in terms of specified embodiments, which are set forth in considerable detail, it should be understood that this by way of illustration only, and that alternative embodiments and operating techniques will become apparent to those skilled in the art in view of the disclosure. For example, other quinone and hydroquinone compounds not specifically disclosed in the text hereof can be used in the process of the present invention, provided that they do not cause a deleterious effect on the selectivity to N-phosphonomethylglycine. Accordingly, modifications can be made without departing from the spirit of the described invention.

What is claimed is:

1. A process for the production of N-phosphonomethylglycine comprising contacting N-phosphonemethyliminodiacetic acid with a peroxide in the presence of a catalyst selected from the group consisting of the salts and salt complexes of cobalt and vanadium, and an effective amount of a quinone or quinone derivative represented by the formulas:

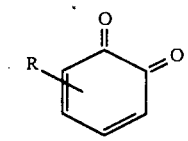

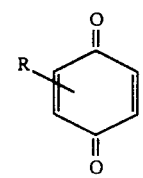

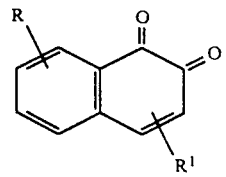

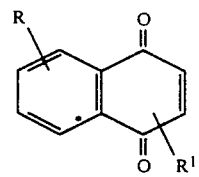

-continued
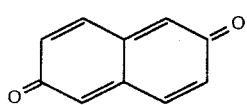 5
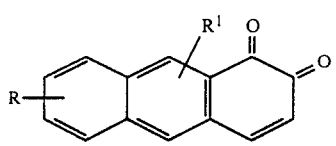 6
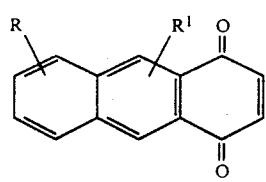 7
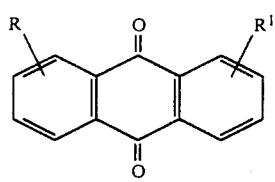 8
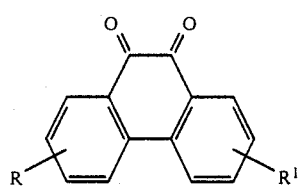 9
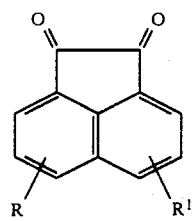 10
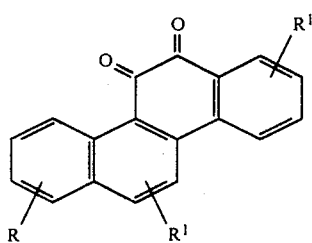 11
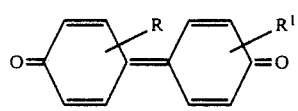 12
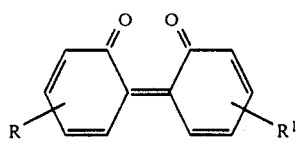 13
-continued
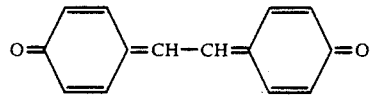 14
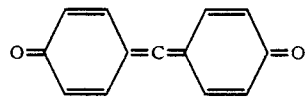 15
and the corresponding hydroquinones:
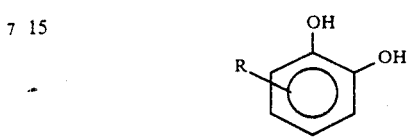 16
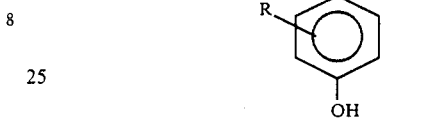 17
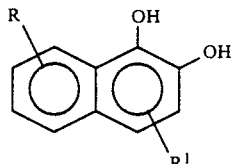 18
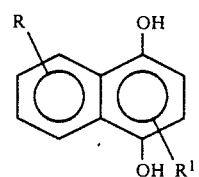 19
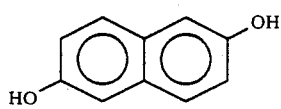 20
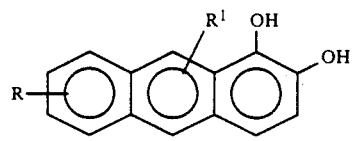 21
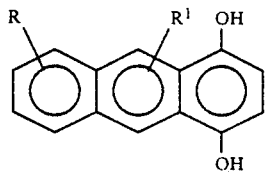 22
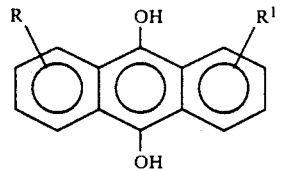 23

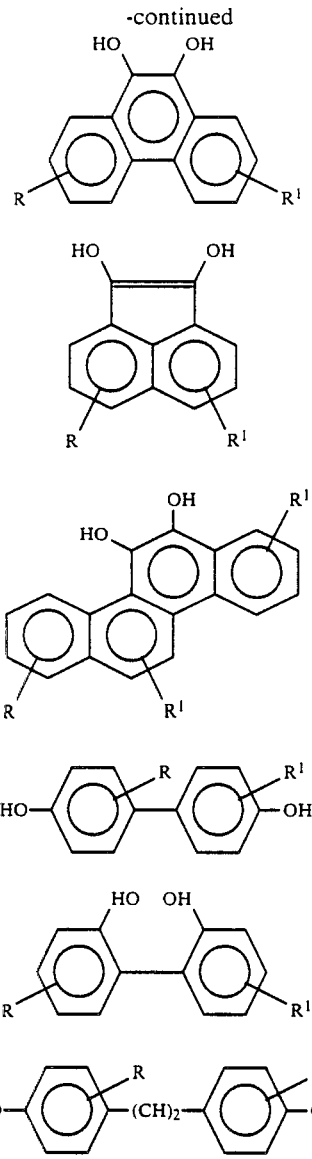

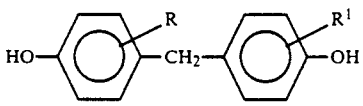

wherein R and R¹ are groups to solubilize the quinone or hydroquinone in the reaction medium.

2. A process of claim 1 wherein R and R¹ are individually selected from the group consisting of hydrogen, halo, sulfonyl, nitro, cyano, quaternary amino groups, hydroxy, carboxy, amino, phosphonic, phosphinic, phosphonium, provided that both R and R¹ cannot be hydrogen.

3. A process of claim 1 wherein the concentration of the quinone or quinone derivative is at least 0.01 molar.

4. A process of claim 3 wherein the catalyst salt concentration is between 0.1 molar and 0.001 molar total metal ion concentration.

5. A process of claim 1 wherein the peroxide is hydrogen peroxide.

6. A process of claim 1 wherein the quinone or quinone derivative is selected from the group consisting of benzoquinone, anthraquinone, napthaquinone and hydroquinone.

7. A process of claim 6 wherein the quinone or quinone derivative is benzoquinone.

8. A process of claim 6 wherein the quinone or quinone derivative is a water soluble anthraquinone.

9. A process of claim 8 wherein the anthraquinone is sulfonated anthraquinone.

10. A process of claim 6 wherein the catalyst is a vanadium salt.

11. A process of claim 6 wherein the catalyst is a cobalt salt.

12. A process of claim 6 wherein the concentration of the quinone or quinone derivative is at least 0.01 molar.

13. A process of claim 6 wherein the catalyst salt concentration is between 0.1 1 molar and 0.5 molar total metal concentration.

14. A process of claims 1 or 13 wherein the N-phosphonomethyliminodiacetic acid is present as a slurry.

* * * * *